US010387931B2

(12) United States Patent
Lee et al.

(10) Patent No.: US 10,387,931 B2
(45) Date of Patent: Aug. 20, 2019

(54) HEALTH TRACKING SYSTEM WITH RESTAURANT MATCHING

(71) Applicant: Under Armour, Inc., Baltimore, MD (US)

(72) Inventors: Chul Lee, San Francisco, CA (US); Yi Qiang, San Francisco, CA (US); Mirela Spasova, San Francisco, CA (US); Mark Allen, San Francisco, CA (US); Poojit Sharma, San Francisco, CA (US); Vaibhav Aggarwal, San Francisco, CA (US); Joohyun Kim, San Francisco, CA (US); Hesamoddin Salehian, San Francisco, CA (US); Hannah O'Neal, San Francisco, CA (US); Layla Martin, San Francisco, CA (US)

(73) Assignee: Under Armour, Inc., Baltimore, MD (US)

( * ) Notice: Subject to any disclaimer, the term of this patent is extended or adjusted under 35 U.S.C. 154(b) by 868 days.

(21) Appl. No.: 14/925,684

(22) Filed: Oct. 28, 2015

(65) Prior Publication Data
US 2017/0124616 A1 May 4, 2017

(51) Int. Cl.
G06Q 30/06 (2012.01)
G06Q 50/12 (2012.01)
G01S 19/42 (2010.01)

(52) U.S. Cl.
CPC .......... G06Q 30/0621 (2013.01); G01S 19/42 (2013.01); G06Q 30/0623 (2013.01); G06Q 50/12 (2013.01)

(58) Field of Classification Search
CPC ........................ G06Q 30/0621; G06Q 50/12
USPC ........................................................ 705/15
See application file for complete search history.

(56) References Cited

U.S. PATENT DOCUMENTS

| 9,070,175 B2* | 6/2015 | Hurst ..................... G06Q 50/12 |
| 9,104,915 B2 | 8/2015 | Conwell | |
| 9,105,041 B2 | 8/2015 | Harman | |
| 2003/0208409 A1* | 11/2003 | Mault ................. G06F 19/3475 |
| | | | 705/15 |
| 2004/0069313 A1* | 4/2004 | DeLaquil ............... G06Q 10/10 |
| | | | 705/15 |
| 2004/0158494 A1* | 8/2004 | Suthar .................... G06Q 30/06 |
| | | | 705/15 |
| 2007/0214052 A1* | 9/2007 | Kao ....................... G06Q 30/02 |
| | | | 705/15 |

(Continued)

Primary Examiner — Florian M Zeender
Assistant Examiner — Christopher R Buchanan
(74) Attorney, Agent, or Firm — Maginot, Moore & Beck LLP

(57) ABSTRACT

A system and method of providing nutritional data for a user is disclosed herein. The method includes receiving a selected restaurant from a personal electronic device, and providing menu data for the user based on the selected restaurant. The method further includes receiving a selected menu item from the personal electronic device, associating the selected menu item with a plurality of food items in a database, and providing the plurality of food items for the user. Furthermore, the method includes receiving a selected one of the plurality of food items from the personal electronic device, and providing nutritional data based on the selected one of the plurality of food items.

14 Claims, 10 Drawing Sheets

(56) References Cited

U.S. PATENT DOCUMENTS

| | | | |
|---|---|---|---|
| 2008/0033827 A1* | 2/2008 | Kuang | G06Q 50/12 |
| | | | 705/15 |
| 2010/0088193 A1* | 4/2010 | White | G06Q 30/0601 |
| | | | 705/26.1 |
| 2012/0233002 A1* | 9/2012 | Abujbara | G06Q 10/06 |
| | | | 705/15 |
| 2013/0325640 A1* | 12/2013 | Morgan | G06Q 50/12 |
| | | | 705/15 |
| 2015/0294292 A1* | 10/2015 | Michishita | G06Q 50/12 |
| | | | 705/15 |
| 2016/0125446 A1* | 5/2016 | Gonen | G06Q 30/0226 |
| | | | 705/14.27 |

* cited by examiner

HEALTH TRACKING SYSTEM WITH RESTAURANT MATCHING

FIELD

This document relates to the field health and fitness tracking devices, and particularly to devices configured to collect and display nutritional information for a user.

BACKGROUND

Health and fitness tracking devices are increasingly utilized by individuals interested in tracking metrics related to their personal health and fitness. These health and fitness tracking devices (which may also be referred to herein as "health tracking devices") typically include a user interface provided on a personal electronic device such as a smartphone, laptop computer, or other computer. The user interface provides the user with any of various health, fitness and activity related data such as food and nutritional consumption, calorie expenditure, heart rate, distance traveled, steps taken, etc. Health tracking devices often use data collected from associated sensors worn by the user, such as heart rate monitors, step counters, stair counters, global positioning system ("GPS") tracking devices, as well as various other motion tracking and biometric monitoring devices. Such sensors are allow the user to easily track and automatically log activity information with the health tracking device. The term "health tracking system" as used herein refers to a health tracking system and/or health and fitness tracking system which includes a health tracking device but which may or may not be used in association with any sensor device.

While activity data is relatively easy to enter into a health tracking device, challenges exist with entry of food and beverage consumption and related calorie and nutritional data (the term "food" as used herein refers to either of or both of foods and beverages). In particular, the user must manually log this data into the health tracking system in order for the system to properly monitor calorie consumption and nutritional health. This process of manually entering food consumption into the system along with calorie and nutritional data is often time consuming and cumbersome. Moreover, it is often difficult for users to accurately determine the calorie and nutritional content of the foods they eat, so the calorie consumption and nutritional data entered into the health tracking system is often inaccurate.

In view of the foregoing, it would be advantageous to provide a health tracking system and related method that allows the user to more quickly and easily enter calorie consumption and nutritional content into a health tracking system. It would also be advantageous if such a system and method provided the user with more accurate calorie consumption and nutritional data for entry into the system in association with foods consumed by the user. Moreover, it would be advantageous if such a system and method could be used to make healthy food choices.

SUMMARY

In accordance with one exemplary embodiment of the disclosure, there is provided a method of providing nutritional data for a user. The method comprises receiving a selected restaurant from a personal electronic device, and providing menu data for the user based on the selected restaurant. The method further comprises receiving a selected menu item from the personal electronic device, associating the selected menu item with a plurality of food items in a database, and providing the plurality of food items for the user. Furthermore, the method comprises receiving a selected one of the plurality of food items from the personal electronic device, and providing nutritional data based on the selected one of the plurality of food items.

Pursuant to another exemplary embodiment of the disclosure, there is disclosed system for providing nutritional data to a user. The system comprises a personal electronic device, a database, and a data processing system. The personal electronic device is configured to (i) provide geo-location data for the user, (ii) display menu items, food items, and nutritional data, and (iii) allow the user to select menu items and food items. The database is configured to store the food items and the nutritional data. The data processing system is configured to (i) receive menu items selected by the user (ii) associate the selected menu items with a plurality of food items, (iii) provide the plurality of food items to the user, (iv) receive a selected food item from the user, the selected food item one of the plurality of food items provided to the user, and (v) provide nutritional data to the user, the nutritional data associated with the selected food item.

In accordance with yet another exemplary embodiment of the disclosure, a non-transient computer readable medium is disclosed containing instructions for providing nutritional data. The computer readable medium contains instructions for providing nutritional data by receiving a selected restaurant from a personal electronic device, providing menu data for the user based on the selected restaurant, receiving a selected menu item from the personal electronic device, and associating the selected menu item with a plurality of food items in a database. After associating the selected menu item with the plurality of food items, the computer readable medium contains instructions for providing the plurality of food items for the user, receiving a selected one of the plurality of food items from the personal electronic device, and providing nutritional data based on the selected one of the plurality of food items.

The above described features and advantages, as well as others, will become more readily apparent to those of ordinary skill in the art by reference to the following detailed description and accompanying drawings. While it would be desirable to provide a health tracking device and associated method that provides one or more of these or other advantageous features, the teachings disclosed herein extend to those embodiments which fall within the scope of the appended claims, regardless of whether they accomplish one or more of the above-mentioned advantages.

DESCRIPTION

Figure 1:
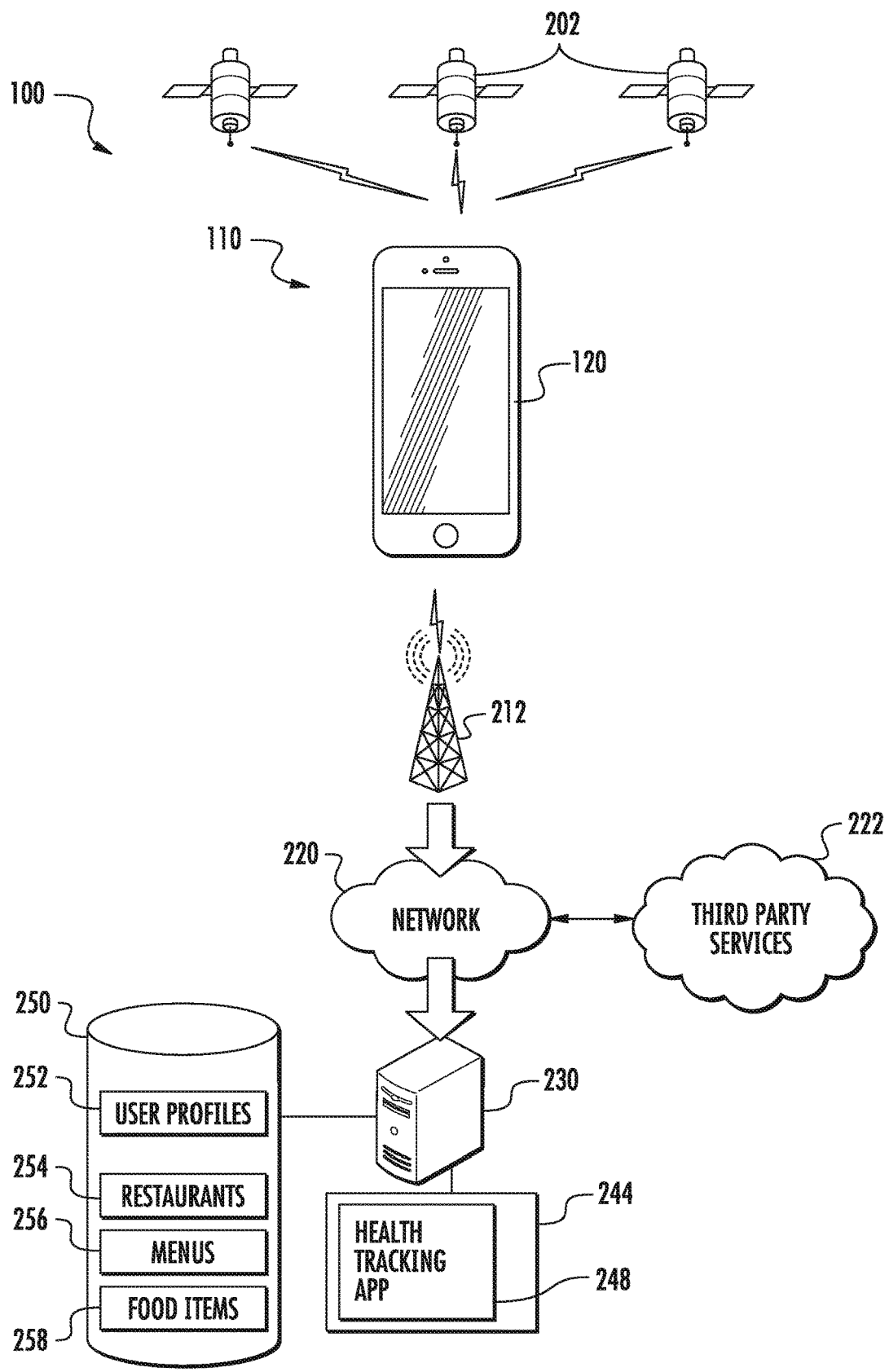
FIG. 1 shows a diagrammatic representation of an exemplary embodiment of a health tracking system including a personal electronics device in communication with a system server.

With reference to FIG. 1, an exemplary embodiment of a health tracking system 100 is shown. The health tracking system 100 includes a personal electronic device 110 configured to communicate with a data processing system such as a system server 230 over a network 220. The personal electronic device 110 is configured to determine a user location and provide the user with information concerning nearby restaurants. The personal electronic device is configured to allow the user to view restaurant menus and select menu items from the restaurant menus. The system server 230 receives the selected menu items from the personal electronic device 110 and matches each selected menu item with a number of food items from an associated database in the memory 234. Matched food items are presented to the user on the personal electronic device 110. The user may select one of the matched food items on the personal electronic device 102 in order to view nutritional information or log food consumption for a particular day.

Personal Electronic Device

The personal electronic device 110 may be provided in any of various forms. A primary example of a personal electronic device 110 configured for use with the health tracking system 200 is a smartphone 120, as shown in FIG. 1. Additional examples of personal electronic devices include handheld or tablet computers, smart watches, laptop computers, portable media players, or any of various other personal electronic devices configured to be carried by the user and capable of communicating with other electronic devices using wireless communications protocols. Accordingly, the term "personal electronic device" generally refers to a portable electronic device configured for wireless communication with other electronic devices. The term "computing device" as used herein refers to personal electronic devices, standalone or stationary computing devices such as desktop computers or other non-portable computers, or mobile computing devices associated with a vehicle occupied by the user. As shown in FIG. 1, the personal electronic devices 110 disclosed herein are generally configured to utilize various communications infrastructures and systems, such as satellites 202 of the global positioning system (GPS), cell towers 212 of a mobile telephony network, and servers and routers of a computer network 220 such as the internet.

Figure 2:
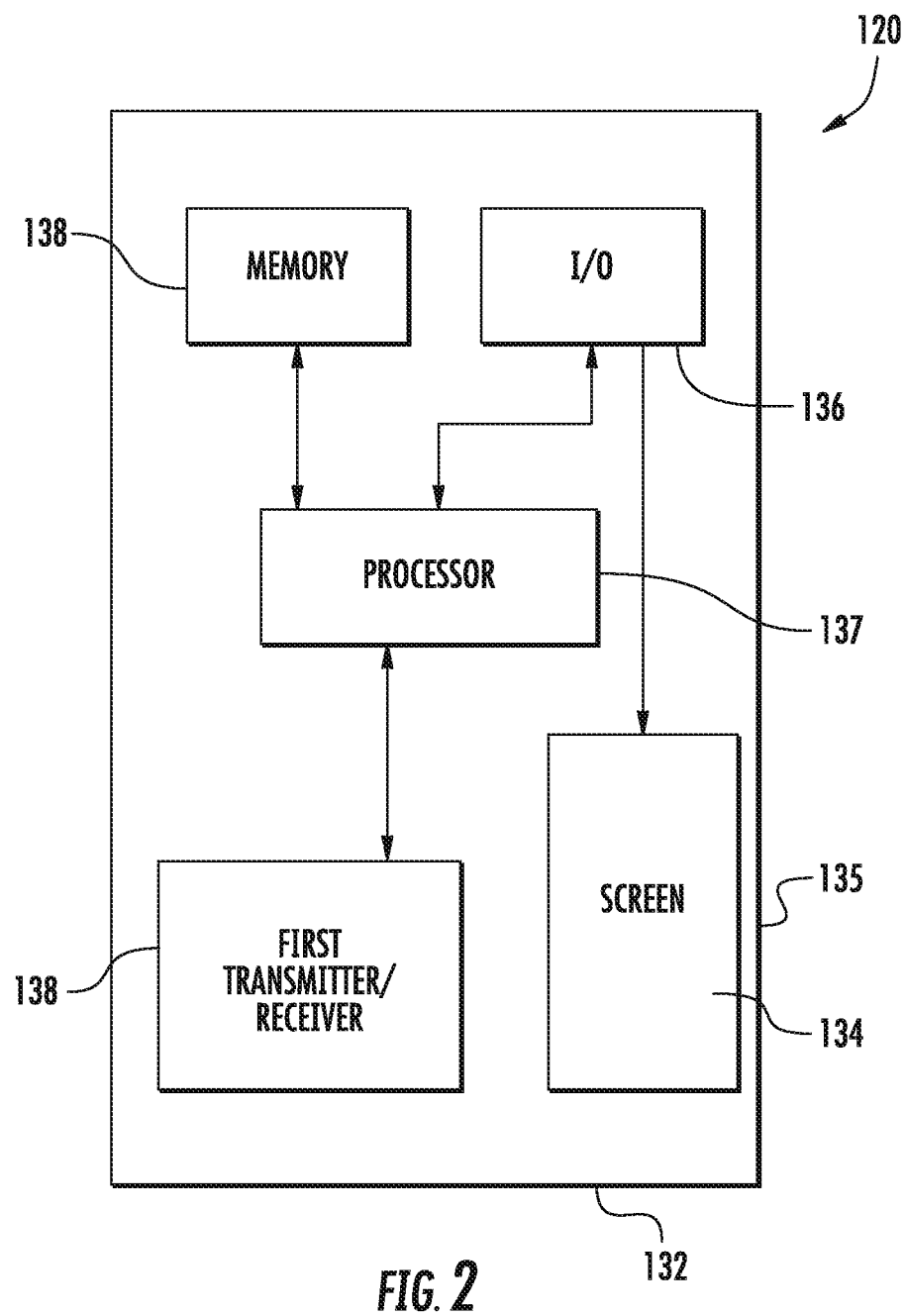
FIG. 2 shows a block diagram of an exemplary personal electronics device for use in association with the health tracking system of FIG. 1.

With reference now to FIG. 2, in at least one embodiment the personal electronic device 110 is a smartphone 120 and includes a display screen 134, an input/output interface 136, a processor 137, a memory 138, and one or more transceivers 139. The smartphone 120 also includes a protective outer shell or housing 132 designed to retain and protects the electronic components positioned within the housing 132. The smartphone 120 also includes a battery (not shown) configured to power the display screen 134, processor 137, transceivers 139 and various other the electronic components within the smartphone 120. As will be recognized by those of ordinary skill in the art, the components of the personal electronic device 110 may vary depending on the type of display device used. Such alternative personal electronic devices may include much of the same functionality and components as the smartphone 120 shown in FIGS. 1 and 2, but may not include all the same functionality or components.

The I/O interface 136 of the smartphone 140 includes software and hardware configured to facilitate communications with the user. The hardware of the I/O interface includes the display screen 134 configured to visually display graphics, text and other data to the user. The display screen 134 of the smartphone 120 may be an LED screen or any of various other screens appropriate for the personal electronic device. In at least one embodiment, the display screen 134 is an LED-backlit touchscreen that allows the user to make selections, type, or otherwise provide input directly on the screen using his or her finger or a stylus device. In addition to the display screen 134, the I/O interface 136 may include additional hardware such as a microphone and speakers to facilitate audio communications with the user.

The processor 137 of the smartphone 120 may be any of various processors as will be recognized by those of ordinary skill in the art. The processor 137 is connected to the I/O interface 136, the memory 138, and the transceivers 139, and is configured to deliver data to and receive data from each of these components. It will be recognized by those of ordinary skill in the art that a "processor" includes any hardware system, hardware mechanism or hardware component that processes data, signals or other information. A processor can include a system with a central processing unit, multiple processing units, dedicated circuitry for achieving functionality, or other systems.

The memory 138 is configured to store information, including data and instructions for execution by the processor 137. The data may include any of various types of data that may be useful to the computing device and any associated applications. In the embodiments disclosed herein, the data may include restaurant data, menu data, food item data, and nutritional data related to foods served at any of various restaurants. The instructions may include a graphical user interface configured to provide a health tracking application on the smartphone 120. Operation of such a health tracking app and exemplary uses of the data is described in further detail below.

The memory 138 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. A computer program product implementing an embodiment disclosed herein may therefore comprise one or more computer-readable storage media storing computer instructions translatable by a processor to provide an embodiment of a system or perform an embodiment of a method disclosed herein. Computer instructions may be provided by lines of code in any of various languages as will be recognized by those of ordinary skill in the art. A "non-transient computer-readable medium" may be any type of data storage medium that can store computer instructions, including, but not limited to the memory devices discussed above.

The at least one transceiver 139 may be any of various transceivers configured for wireless or wired communication with other electronic devices, including the ability to send communication signals and receive communication signals. The transceivers 139 may include different types of transceivers configured to communicate with different networks and systems. Such transceivers are well known and will be recognized by those of ordinary skill in the art. The transceivers typically perform wireless communications. However, in at least one embodiment, the transmitters may be used in association with data ports requiring a physical (i.e., wired) connection to another device prior to transmission of the data.

In at least one embodiment, the transceivers 139 are configured to allow the smartphone 120 to perform wireless communications with a wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements.

In the embodiment disclosed herein, the transceivers 139 further include GPS receivers configured to receive GPS signals from GPS satellites 202. Accordingly, the smartphone 120 or other personal electronic device may be a geo-position enabled device configured to determine its location based on received signals utilized by the health tracking system 100. While the smartphone 120 is described herein as being a GPS-enabled device, it will be appreciated that in other embodiments, other geo-position devices may be provided utilizing signals and technologies other than GPS.

In addition to transceivers configured to communicate with the cellular towers 212 of a wireless telephony network, and receive signals from GPS satellites 202, the transceivers 139 may also be configured to communicate with any of various other electronics devices and networks using any of various communication schemes. For example, the transceivers 139 may also be configured to allow the smartphone 120 to communicate with any of various local area networks using WiFi, Bluetooth® or any of various other communications schemes.

In at least one embodiment, the smartphone 120 is configured to collect sensor data from one or more sensors which are associated with the user. Such sensors may include sensors worn or carried by the user separate from the smartphone 120, or sensors included on the smartphone 120. Exemplary sensors may include heart rate monitors, accelerometers, breathing sensor, temperature sensors, or any of various other sensors typically associated with athletic activity. Exemplary sensor data may include heart rate, power, motion, movement, speed, range, distance, acceleration data, etc. Sensor data may include physiological data (e.g., heart rate, breathing rate, temperature, etc.) or contextual readings or calculations (e.g., distance traveled, acceleration, etc.), or estimates of such associated with various physical activities of the user.

Data Processing System

Figure 3:
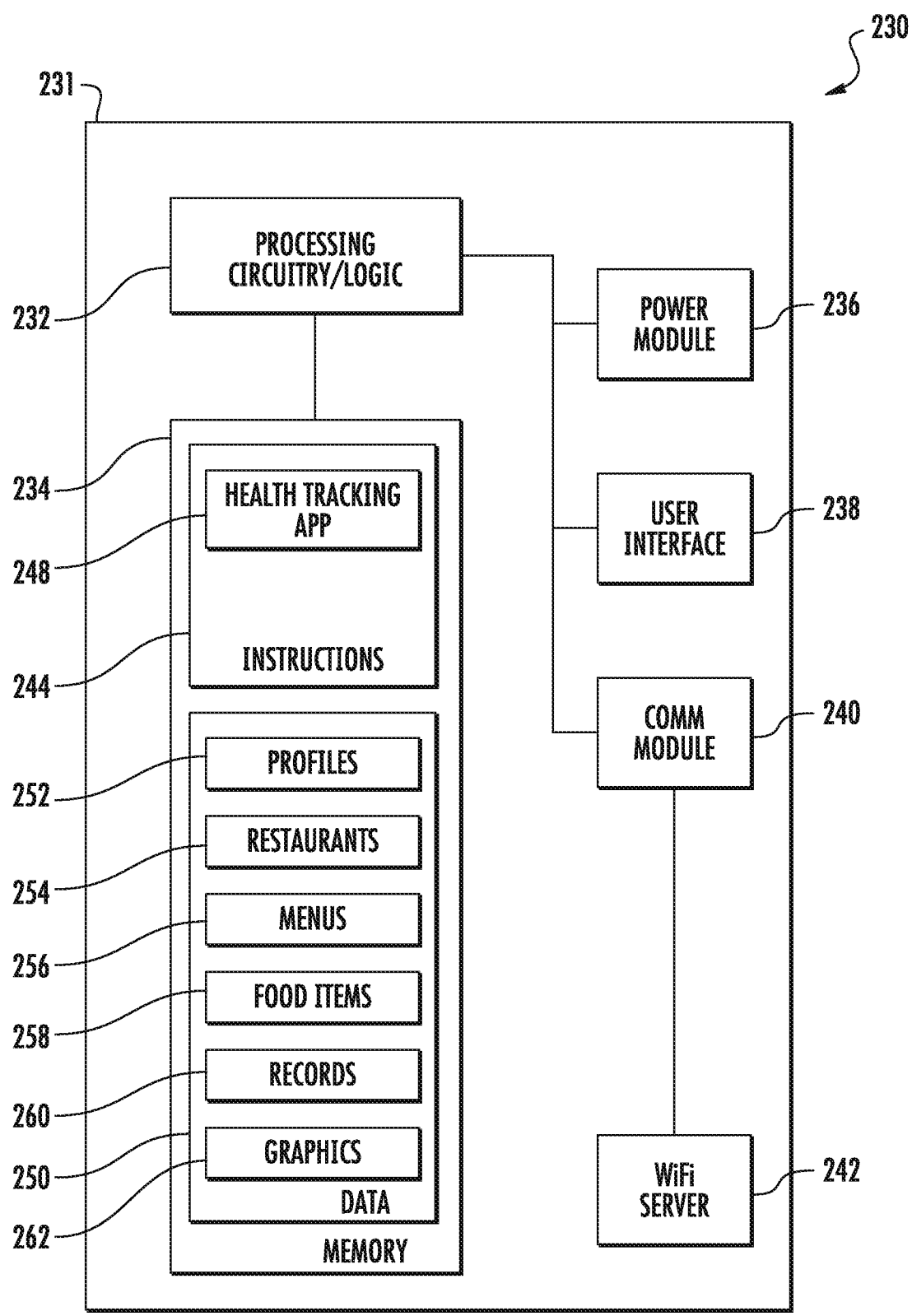
FIG. 3 shows a block diagram of an exemplary system server for use in association with the health tracking system of FIG. 1.

With reference now to FIG. 3, a block diagram of an exemplary embodiment of the system server 230 of FIG. 1 is shown. It should be appreciated that the embodiment of the system server 230 shown in FIG. 3 is only one exemplary embodiment of a system server 230. As such, the exemplary embodiment of the system server 230 of FIG. 3 is merely representative of any of various manners or configurations of system servers or other data processing systems that are operative in the manner set forth herein.

The system server 230 of FIG. 3 is typically provided in a housing, cabinet or the like 231 that is configured in a typical manner for a server or related computing device. The system server 230 includes processing circuitry/logic 232, memory 234, a power module 236, a user interface 238, a network communications module 240, and a wireless transceiver 242.

The processing circuitry/logic 232 is operative, configured and/or adapted to operate the system server 230 including the features, functionality, characteristics and/or the like as described herein. To this end, the processing circuit 232 is operably connected to all of the elements of the system server 230 described below. The processing circuitry/logic 232 is typically under the control of program instructions 244, programming software or firmware contained in memory 234. The program instructions include a health tracking app 248 as explained in further detail below. In addition to storing the instructions 244, the memory 234 also stores data 250 for use by the collection app 244. The data 250 includes user profiles 252, restaurant database 254, a menu database 256, a food items database 258, records 260 and graphics.

With continued reference to FIG. 3, the power module 236 of the system server 230 is operative, adapted and/or configured to supply appropriate electricity to the system server 230 (i.e., including the various components of the system server 230). The power module 236 may operate on standard 120 volt AC electricity, but may alternatively operate on other AC voltages or include DC power supplied by a battery or batteries.

The network communication module 240 of the system server 230 allows for communication with any of various devices using various means. In particular, the network communications module 240 includes a wide area network port that allows for communications with remote computers over the internet (e.g., network 220 of FIG. 1). The network communications module 240 further includes a local area network port that allows for communication with any of various local computers housed in the same or nearby facility. In at least one embodiment, the local area network port is equipped with a WiFi server 242 or other wireless communications device. Accordingly, it will be appreciated that communications with the system server 230 may occur via wired communications or via the wireless communications. Communications may be accomplished using any of various known communications protocols. In the embodiment of FIG. 3, the wireless transceiver is identified as a WiFi transceiver 242, but it will be recognized that the wireless transceiver could use a different communications protocol.

The system server 230 may be accessed locally. To facilitate local access, the system server 230 includes an interactive user interface 238. Via interface 228, the user may access the instructions, including the health tracking app 248, and may collect data from and store data to the memory 234. In at least one embodiment, the user interface 238 may suitably include an LCD type screen or the like, a mouse or other pointing device, a keyboard or other keypad, speakers, and a microphone, as will be recognized by those of ordinary skill in the art. Accordingly, the user interface 238 is configured to provide an administrator or other authorized user with access to the memory 234 and allow the authorized user to amend, manipulate and display information contained within the memory.

As mentioned above, the memory 234 includes various programs and other instructions 244 that may be executed by the processor 232. In particular, the memory 234 of the system server 230 of FIG. 3 includes the health tracking application 248. The health tracking app 248 is configured to control the system server 230 in order to allow a human to obtain nutritional data related to any of various food items. Execution of the health tracking application 248 by the processor 232 results in signals being sent to and received from the user interface 238 and the communications module 240 to allow a user receive and update the information in the food items database 258. Various aspects of the food items database 258 are explained in further detail below. The health tracking app 248 is configured to provide various graphical views and screen arrangements to be displayed to a user on a personal electronic device 110. Examples of such screens for display on a personal electronic device 110 are provided in FIGS. 4-9, as discussed in further detail below. While a brief description of various features of the exemplary health tracking app 248 is provided in the paragraphs below, it should be appreciated that the health tracking system 100 described herein is only an exemplary form or configuration for the health tracking system.

With continued reference to FIG. 3, in addition to the instructions 244, the memory 224 also includes data 250. The data 250 includes user profiles 252, a restaurants database 254, a menus database 256, a food items database 258, records 260, and graphics 262.

The user profiles 252 includes a profile data for each user of the health tracking system 100. Each user profile includes demographic information for the users such as name, age, gender, height, weight, performance level (e.g., beginner, intermediate, professional, etc.) or other information for the user.

The restaurants database 254 includes restaurant data. The restaurant data may include any of various types of information concerning restaurants such as restaurant name, geographic location (e.g., longitude latitude data), restaurant type (e.g., bar, fast food, fine dining, Mexican food, Chinese food, sandwich shop, etc.), and restaurant menus (e.g., breakfast, lunch, dinner, drinks, desserts, etc.). As explained in further detail below, the user may be presented with restaurant data based on any of various conditions, such as user proximity to the restaurant, a search for the restaurant name or type, etc. The user may select a particular restaurant from the restaurant data. While FIGS. 1 and 3 show the restaurants database 254 as being provided on the system server 230, it will be recognized that in alternative embodiments the restaurants database 254 may be provided at any of various locations, including third party databases and related remote memory locations. In at least one embodiment, the health tracking app 248 is configured to access such third party databases using third party services 222 available via the network 220, as shown in FIG. 1. In such embodiment, the health tracking app 248 may utilize any number of application programming interfaces (APIs) to access the data in the third party databases and incorporate such information for use in the health tracking app 248. In some embodiments, and depending on available licenses, the data obtained using the third party services 222 (including restaurant data) may be copied and saved to the memory 234 of the system server 230 such that a partial or complete copy of the remote restaurants database is maintained on the system server 230. In other embodiments, each time data from the remote memory location is needed, the health tracking app 248 uses the appropriate APIs to gather the required information from the third party databases. Any of various third party service providers and associated restaurant databases and APIs may be used by the health tracking app to obtain the restaurant data. Examples of such third party service providers capable of providing restaurant data include Foursquare Labs, Inc. of New York, N.Y., and Yelp, Inc. of San Francisco, Calif. In at least one embodiment, restaurant information may also be provided by individual restaurants.

The menus database 256 includes restaurant menus and associated menu items for each restaurant in the restaurant database 254. The term "menu item" as used herein refers to data associated with a particular listing on a particular restaurant menu. Menu items are not editable by users of the health tracking system, and may only be edited by authorized personnel having editing privileges within the menus database 256. Each menu includes some number of menu items, and may also include menu categories or headings. For example, if a restaurant has a dinner menu, that dinner menu may include seven menu items under the "Appetizer" heading, five menu items under the "Salad" heading, ten menu items under the "Sides" heading, and eight menu items under the "Entrées" heading. Data is retained in the menus database 256 for each menu item. For example, the menus database 256 may include a name for the menu item (e.g., "Chicken Cobb Salad"), a brief listing of additional information for the menu item (e.g., "500 calories"), a photo of the menu item, or other information intended to quickly convey information about the menu item to the user. As explained in further detail below, after the user chooses a menu to view (e.g., the "Dinner Menu"), the user may then select one of the menu items from such menu. While FIGS. 1 and 3 show the menus database 256 as being provided on the system server 230, it will be recognized that in alternative embodiments the menus database 256 may be provided at any of various locations, including third party databases and related remote memory locations. In at least one embodiment, the health tracking app 248 is configured to access such third party databases using third party services 222 available via the network 220, as shown in FIG. 1. In such embodiment, the health tracking app 248 may utilize any number of APIs to access the data in the third party databases and incorporate such information for use in the health tracking app 248. In some embodiments, and depending on available licenses, the data obtained using the third party services 222 (including the menu items) may be copied and saved to the memory 234 of the system server 230 such that a partial or complete copy of the remote menus database is maintained on the system server 230. In other embodiments, each time data from the remote memory location is needed, the health tracking app 248 uses the appropriate APIs to gather the required information from the third party databases. Any of various third party service providers and associated restaurant databases and APIs may be used by the health tracking app to obtain the restaurant data, including the exemplary third party service provides discussed above in association with the restaurants database. In at least one embodiment, menu information may also be provided by individual restaurants.

The food items database 258 includes a plurality of food items. The term "food item" as used herein refers to data associated with a food that may be consumed by a user. As explained in further detail below, in at least one embodiment, each food item may be either a "food" or a "recipe". Food items are editable by users or may be created by users within the food items database 258 without the need for special authorization or privileges. In at least one embodiment, each of the food items includes a name for the food item, summary information about the food item, and detailed nutritional information about the food item. Detailed information about a food item may include one or more of serving size, calories, ingredients, or any other nutritional information about the food item. For example, the nutritional information may include information that may be provided on a USDA food labels or state-regulated food labels (e.g., vitamin and mineral content, fat content, cholesterol content, protein content, sugar content, carbohydrate content, fiber content, organic contents, etc.). The summary information about the food item may include some subset of the more detailed information about the food item. For example, the summary information about the food item may only include serving size and calorie information. The data associated with a food item is typically more detailed than the data associated with a menu item. In particular, food items typically include more detailed nutritional information than menu items. Additionally, food items in the food items database 258 may be differentiated from menu items in the menus database 256 because the food items database 258 is editable by users, as explained above, while the menus database 256 is not editable by users. Accordingly, food items are editable by users and/or may be created by users without special authorization, while menu items are only editable by a system administrator or other authorized personnel. Therefore, it will be recognized that in at least some embodiments, food items in the food items database 258 may have been entered by any of various sources including the administrator of the health tracking system 100, commercial food providers (e.g., restaurant owners), and users of the health tracking system 100.

While the data maintained for menu items in the menus database 256 may resemble the data maintained for food items in the food items database 258, no menu item is exclusively associated with a single food item. Instead, as explained in further detail below, the system server matches a number of food items in the food items database 258 with a menu item selected by the user. While no menu item is exclusively associated with a single food item, the number of times a food item is matched with a menu item and then selected by a user is also maintained as data within the memory of the system server 230 or other data processing system. The number of times that a food item has been selected by a user in association with a menu item may then be used by the system 100 to determine whether a food item should be a match with a selected menu item when determining future matches for the menu item.

The records 260 include current and historical data stored by the system server 230 in association with operation of the system server 230, execution of the health tracking app 248, and manipulation of data 250 within the memory 234. For example, the records 260 may include information concerning amendments made to any of various food items 258. The records 260 may also include other information related to the control and operation of the system server 230, including statistical, logging, licensing, and historical information. In at least one embodiment, the records 260 may also include a food diary/log for each user. The food diary/log allows the user to track food consumed by the user over a period of days and any nutritional data associated with the food consumed. For example, the food diary/log may allow the user to enter particular food items consumed by the user and keep track of the associated calories, sugar, carbohydrates, protein, or any of various other nutritional data associated with the food items entered by the user in the food diary/log.

The graphical views 262 provide various screen arrangements to be displayed to the user in on a personal electronic device 110, as shown in FIG. 1. Examples of such screens for display on a personal electronic device 110 are provided in FIGS. 4-9, discussed in further detail below.

While the system server 230 has been explained in the foregoing embodiment as housing the health tracking application 248 and the various records and databases in the memory 234, it will be recognized that these components may be retained in other locations in association with the health tracking system 100. For example, in at least one embodiment, the restaurant database 254 and the menu database 256 may be data retained by a third party database separate from the system server 230. In such embodiment, the health tracking app may utilize any number of APIs to access the data in the third party databases and incorporate such information for use in the health tracking app 248. Accordingly, it will be recognized that the description of the system server 230 of FIG. 3 is but one exemplary embodiment of a data processing system that may be utilized by the health tracking system 100.

Health Tracking App

With reference now to FIGS. 4-9, several exemplary screen shots of view controllers for the health tracking app are shown. The view controllers are made available at the system server 230 and presented to users on their personal electronic devices 110 via the network 220. The view controllers include a restaurant search view controller 400 (see FIG. 4), a restaurant menu view controller 500 (see FIGS. 5-6), a restaurant food summary view controller (see FIGS. 7-8), and a food nutrition details view controller (see FIG. 9). While FIGS. 4-9 show various view controllers of the health tracking app 248 that are associated with nutrition and diet tracking features, it will be recognized that in at least some embodiments the health tracking app 248 may also include additional features, such as activity tracking, sleep tracking, or other features which may be associated with health tracking apps, as will be recognized by those of ordinary skill in the art.

Figure 4:
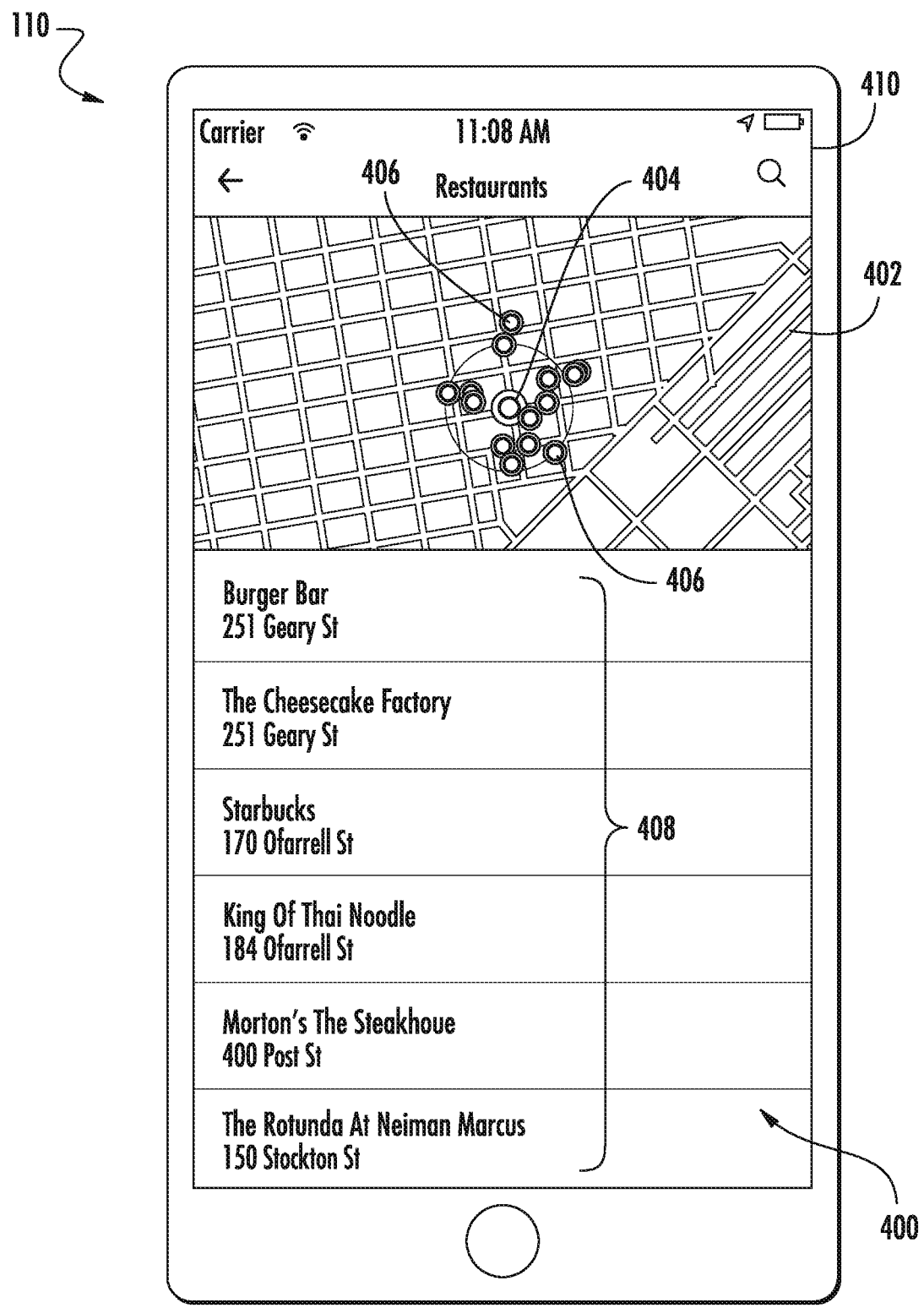
FIG. 4 shows an exemplary screen shot of a restaurant search view controller provided by a health tracking application of the health tracking system and displayed on the personal electronics device of FIG. 2.

With particular reference now to FIG. 4, in at least one embodiment, the restaurant search view controller 400 is provided on the screen of a personal electronic device 110. The restaurant search view controller 400 includes a map 402 showing the region where the user is currently located based on GPS data received from the personal electronic device 110. The user's current location on the map is shown at mark 404 and a number of nearby restaurants are shown by marks 406. The restaurants noted by marks 406 are listed individually by name and address in the table listing 408 under the map 402. In at least one embodiment, each of the marks 406 on the map may include a reference designator (e.g., A, B, C, D, etc.), and the reference designator may be displayed next to the restaurant in the table listing to assist the user in determining the exact location of each restaurant on the map 402.

The restaurants shown on the map 402 are retrieved from the restaurants database 254 based on the location of the user and any of various additional parameters defined within the health tracking app 248. For example, the restaurants shown on the map 402 may limited to a predetermined number of restaurants closest to the user's current position (e.g., the closest ten, fifteen or twenty restaurants). Alternatively, if the user is interested in visiting a particular restaurant or a particular genre of restaurant, the user may use the search feature by selecting the search icon 410 and entering a particular restaurant name or genre of restaurant (e.g., "Starbucks" or "Coffee"). When the user makes use of the search feature, the health tracking app searches the restaurants database 254 based on the search terms entered by the user and returns a limited number of restaurants in the table listing 408 that are most closely associated with the search terms entered by the user. After reviewing the table listing 408, the user may select one of the listed restaurants to indicate he or she would like to see a menu from the selected restaurant. The selection may be made from the map 402 or from the table listing 408.

Figure 5:
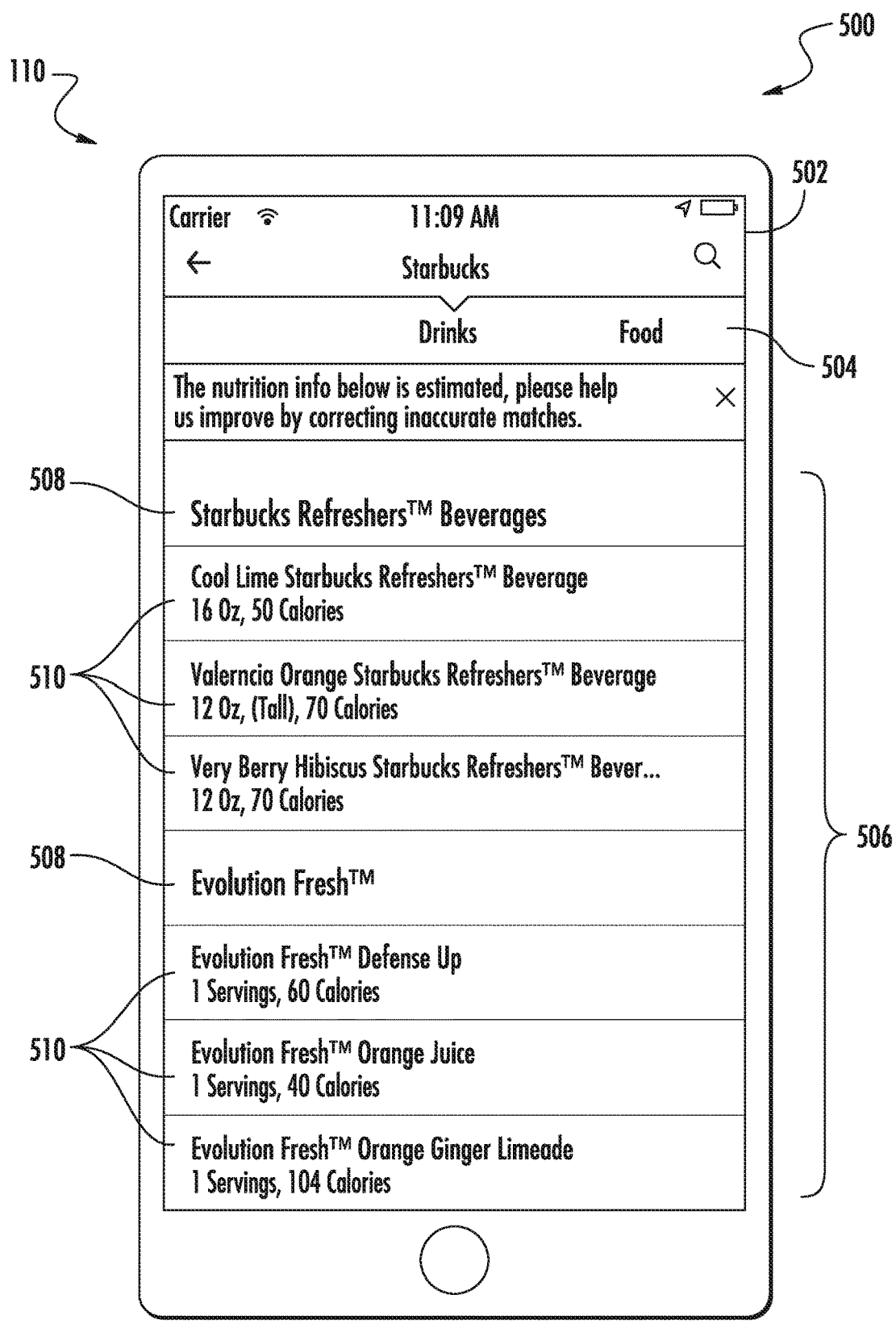
FIG. 5 shows an exemplary screen shot of a restaurant menu view controller provided by the health tracking application and displayed on the personal electronics device of FIG. 2.

With reference now to FIG. 5, after selecting a restaurant from the restaurant search view controller 400, the user is presented with the restaurant menu view controller 500 on the personal electronic device 110. Alternatively, if it is determined that a user is actually within the premises of a restaurant (based on GPS data) or within a predetermined proximity of a restaurant (e.g., within 10 yards), the user is automatically presented with the restaurant menu view controller without the need for the user to select any of the restaurants listed in the table listing 408. In this manner, the health tracking system 100 is advantageously configured to automatically provide the user with information which he or she is most likely interested in based on the current location of the user.

As shown in the example of FIG. 5, the user has selected "Starbucks" from the table listing 408 (or is within the premises of or a predetermined distance from the restaurant), and the restaurant menu view controller 500 is presented to the user. The restaurant menu view controller 500 includes a title block 502, a menu block 504, and a menu listing 506. The title block 502 shows the name of the restaurant (i.e., "Starbucks") that the user has selected or which the user is within the predetermined proximity of. The menu block 504 shows the various menus for the restaurant that are available for viewing. In this case, Starbucks includes a "Drinks" menu and a "Food" menu, and the user has selected the "Drinks" menu for viewing. The menu listing 506 may include various menu headings 508. In the example of FIG. 5, the menu headings 508 include, inter alia, "Starbucks Refreshers™ Beverages" and "Evolution Fresh™". The menu items 510 are listed below each menu heading 508. Each menu item includes a name and may also include a limited amount of nutritional information for the menu item as contained within the menus database 256. In this case, each menu item 510 includes an associated serving size (e.g., 16 oz.) and an associated number of calories for the serving size (e.g., 50 calories).

As the user scans the menu items 510, the health tracking app 248 searches for "matches" for each listed menu item 510 in the food items database 258. Each "match" is an entry in the food items database 258 that more closely resembles the menu item than other entries in the food items database 258. Accordingly, some limited number of matches is determined for each menu item 510 presented to a user (e.g., three matches, five matches, ten matches, etc., of food items from the food items database 258 may be matched with each menu item 510). The process of matching a number of food items with a menu item may be determined according to any of various algorithms and methods. For example, in at least one embodiment, the process of matching may be dependent exclusively on the similarities between the names of the menu item and the food item. Alternatively, in at least one embodiment, the process of matching is dependent at least in part on the number of times the food item has been previously matched with the menu item, or the number of times other users have selected the food item when the food item is presented to the user in association with the menu item. In this manner, a type of crowd sourcing may be used in the matching process. In additional embodiments, other parameters such as nutritional content may be used in the matching process. Also, some weighting of parameters may be used during the matching process. For example, in considering the foregoing examples, similarity in name for the menu item and the food item may be most highly weighted, followed by previous matching being moderately weighted, and nutritional content similarities may be lower weighted. Accordingly, it will be recognized that the matching process may occur using any of various different algorithms and methods. In at least one embodiment, matches returned by the health tracking app 248 for a selected menu item are based at least in part on one or more of: (i) previous selected matches for the menu item, (ii) the location of the user (e.g., is the user in a particular restaurant or close to a particular restaurant), (iii) the menu selected by the user, and/or (iv) a correlation between the name of the selected menu item and the title of a food item.

While matching occurs as the user views the menu listing 506, the matches returned from the matching process are not presented to the user until the user actually selects one of the menu items 510 that he or she is interested in purchasing or has already purchased. In this manner, the system 100 is configured to compute matches while the user scrolls through a menu, such that the system is able to present the matches to the user more quickly upon selection of a menu item. An exemplary illustration of the matches presented to the user after selecting a menu item 510 from the menu listing 506 is described in further detail below with reference to FIG. 6.

While the current example of FIG. 5 describes a situation wherein the user has selected a restaurant with a number of menus, in some situations the user may select a restaurant that does not have a menu. In these situations, the restaurant menu view controller of FIG. 5 is not presented to the user. Instead, the health tracking system 100 proceeds with matching the restaurant name to a number of food items, as shown in FIG. 6.

Figure 6:
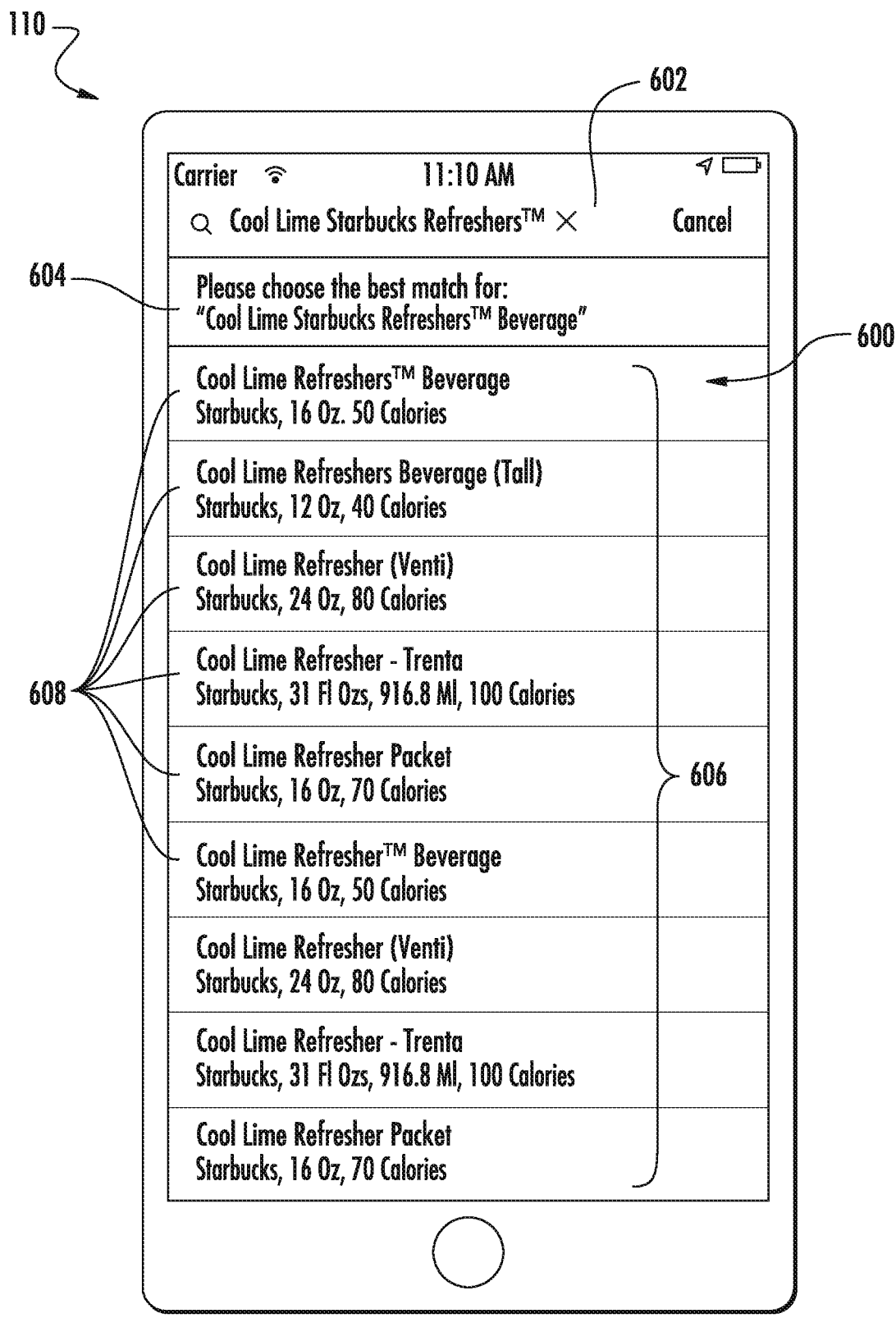
FIG. 6 shows an exemplary screen shot of a match page of the restaurant search view controller provided by the health tracking application and displayed on the personal electronics device of FIG. 2.

With reference now to FIG. 6, after the user selects a menu item from the restaurant menu view controller 500 (or if no menu is available, after the user selects a restaurant from the restaurant search view controller 400), the health tracking app 248 provides a match page 600. The match page 600 includes a selected menu item block 602, an instruction block 604, and a listing block 606 including a number of matches 608 from the food items database 258. In the example of FIG. 6, the selected menu item listed in the menu item block 602 is the "Cool Lime Starbucks Refreshers™" product from the Starbuck's Drink menu. The listing block 606 includes a number of matching food items 608 from the food items database 258. The instruction block 604 instructs the user to choose the best match in the listing block 606 for the selected menu item. In the example of FIG. 6, each of the different food items includes a "Cool Lime Refreshers" beverage, but each of the different food items is of a different serving size. Accordingly, the user selects the match 608 in the listing block 606 that best represents the drink that the user has purchased and consumed or is interested in purchasing and consuming.

Figure 7:
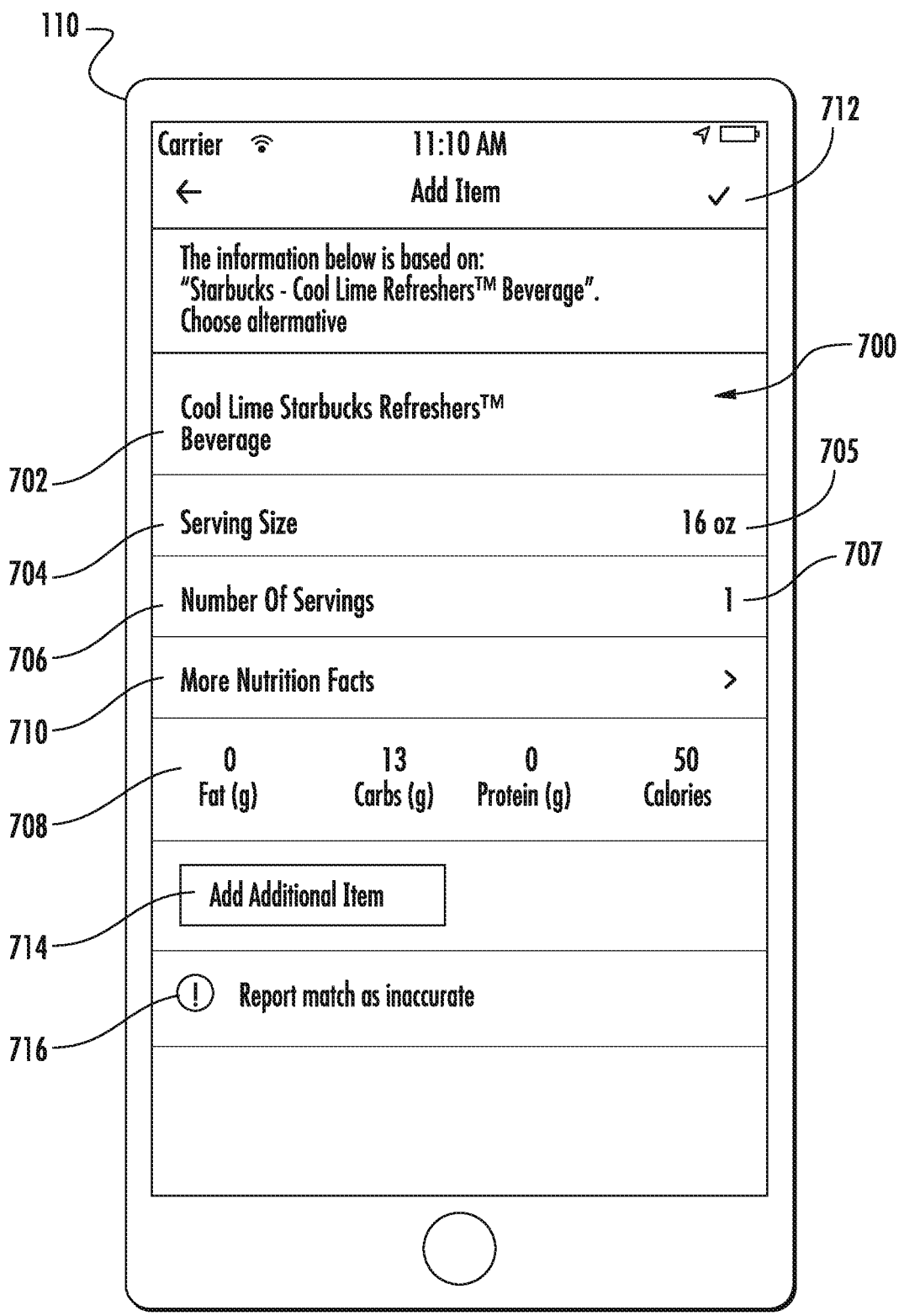
FIG. 7 shows an exemplary screen shot of a food summary view controller provided by the health tracking application and displayed on the personal electronics device of FIG. 2.

With reference now to FIG. 7, after the user selects one of the matches 608, the user is presented with a food summary view controller 700. The food summary view controller 700 includes a selected match block 702, a serving size block 704, a number of servings block 706, a nutrition summary block 708, a more nutrition facts link 710, an add item option 712, an "Add Additional Food Item" option 714, and a "Report Match" option 716. The selected match block 702 shows the name of the food item that the user selected from the match page 600. The serving size block 704 shows the serving size of the selected match (e.g., 16 oz.). The number of servings block 706 lists the number of servings the user consumed or intends to consume (e.g., 1 serving). The nutrition summary block 708 lists a summary of nutrition facts for the selected food item (e.g., fat content, carbohydrates, protein, sugar, calories, etc.). If the desired nutritional data is not shown in the nutritional summary block 708, the user may select the more nutrition facts link 710, and review additional nutritional data, similar to the data shown in FIG. 8, described in further detail below.

With continuing reference to FIG. 7, if the user finds the information displayed accurate for a food item that he or she has consumed or intends to consume, the user may add the food item to a consumption log or diary by selecting the "Add Item" option 712. This will cause the health tracking application 248 to add the food item to the user's food consumed for the day. On the other hand, if the user wishes to modify the food item, the user may do so in the food summary view controller 700. For example, in the embodiment of FIG. 7, the serving size block 704 and number of servings 706 are both editable by the user. Thus, if the user consumed a 20 oz. serving of the food item, the user simply taps the "16 oz" entry 705 in the serving size block 704 of FIG. 7, and a text box appears allowing the user to change the serving size from "16 oz." to "20 oz". Similarly, if the user consumed two servings instead of one of the listed food item, the user simply taps the "1" entry 707 in the number of servings block 706, and a text box appears allowing the user to change the number of servings consumed from "1" to "2".

After amending the food item by changing either the entry in the serving size block 704 or the number of servings block 706, the user may enter the amended food item as a new item in the food items database 258 by selecting the "Add Additional Food Item" option 714. When this option 714 is selected, the food items database 258 is updated to include the amended food item as a new item. As an example, if the serving size of FIG. 7 is amended from "16 oz" to "20 oz", the user may select the "Add Additional Food Item" option 714 to add the entry as a new food item in the food items database 258. As a result, the food items database will include at least two food items with the "Cool Lime Starbucks Refreshers™ Beverage" name, one being a 16 oz version and the other being the new 20 oz version.

In addition to the above, if the user believes that a particular food item presented to the user on the food summary view controller 700 is inaccurate for some reason, the user may choose the "Report Match as Inaccurate" option 716. By selecting this option, the user can submit an entry requesting the system administrator to review a particular item in the food items database as being inaccurate. For example, if Starbucks does not offer a 16 oz version of the "Cool Lime Refreshers™ Beverage", the user may select the "Report Match as Inaccurate" option 716 and make a note to the system administrator requesting the food items database to be amended for the reason provided.

Figure 8:
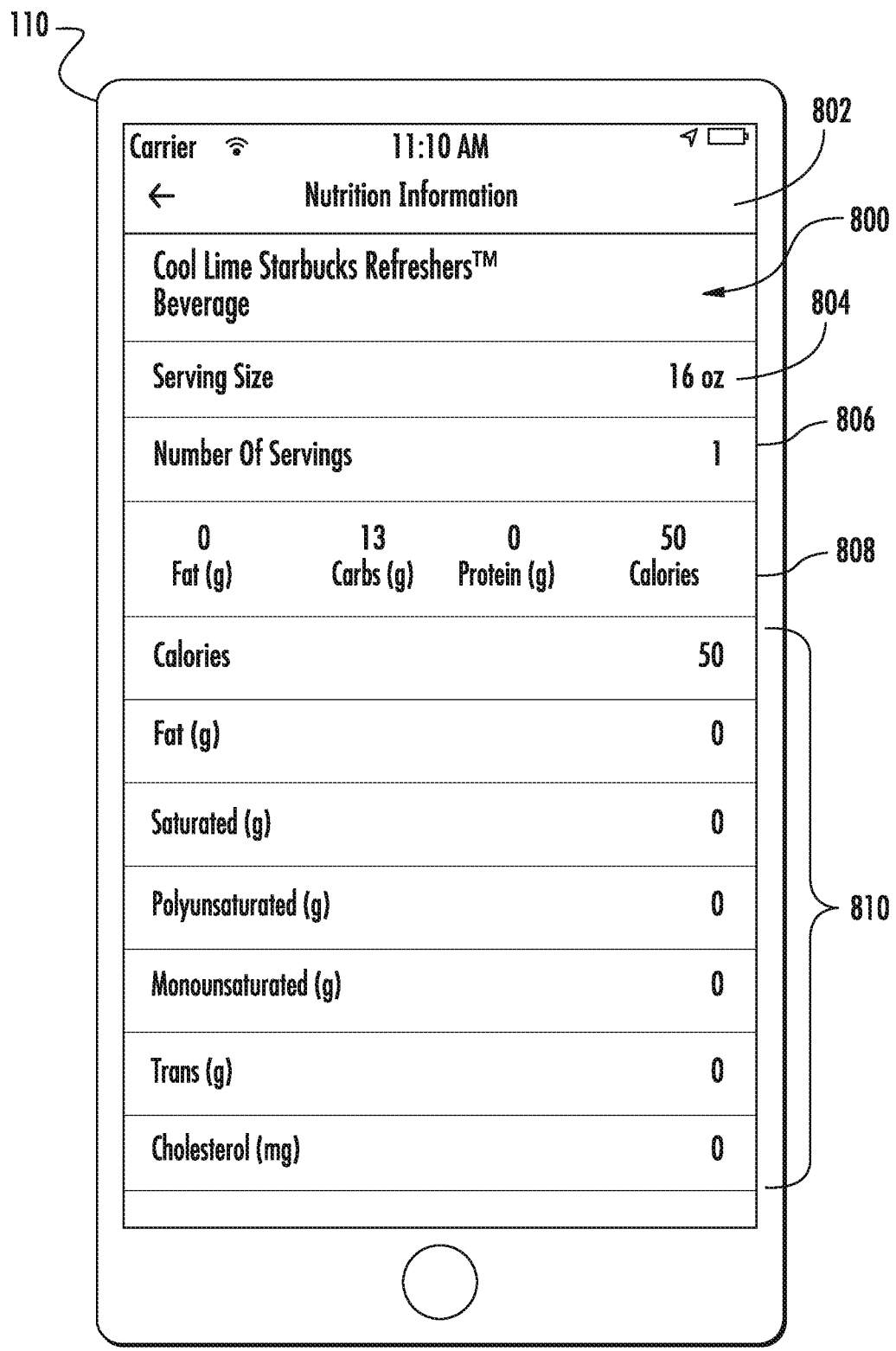
FIG. 8 shows an exemplary screen shot of a restaurant nutrition view controller provided by the health tracking application and displayed on the personal electronics device of FIG. 2.

As noted above, if the user wishes to obtain even more nutritional information for the selected food item, the user may select the more nutrition facts link 710, as shown in FIG. 7. If the user selects this link 710, the user is presented with even more nutritional facts for the selected food item in a restaurant nutrition details view controller. For example, FIG. 8 shows a restaurant nutrition view controller 800 presented to the user following selection of the more nutrition facts link 710 of FIG. 7. The restaurant nutrition view controller 800 includes a selected match block 802, a serving size block 804, a number of servings block 806, a nutrition summary block 808, and an additional nutrition facts table 810. The selected match block 802, the serving size block 804, the number of servings block 806, and the selected nutrition summary block 808 function in the same way as the associated blocks 702, 704, 706 and 708 operate, as described above. However the additional nutrition facts table 810 provides additional nutrition information that is not provided in the nutrition summary block 808. This additional nutritional information may include any of various types of more specific nutritional information such as vitamin content, fat content, cholesterol content, fiber content, protein content, or any of various additional types of nutritional information as will be recognized by those of ordinary skill in the art.

As noted previously, in at least one embodiment, each food item in the food items database 258 may be provided as a "food" or a "recipe". A "food" is defined in a manner such that it cannot be parsed into a list of ingredients (e.g., "chicken sandwich," without a detailed list of the ingredients on the chicken sandwich). While a "food" may have a serving size (e.g., one, two, etc.), the user does not have the ability to edit the food to remove any particular part of the food item (e.g., the bread cannot be removed from the chicken sandwich) or add anything to the food item. On the other hand, a "recipe" is defined in a manner such that it may be parsed into a list of ingredients (e.g., bread, chicken, lettuce, tomato, mayo, mustard, peppers, etc.). Accordingly, a recipe is editable by the user to remove any particular ingredient (e.g., remove bread from the chicken sandwich) or add a particular ingredient (e.g., add mayonnaise to the chicken sandwich). Therefore, "foods" may be considered "unitary" (or "homogeneous") in nature, while "recipes" are "multi-component" (or "heterogeneous") in nature.

Figure 9:
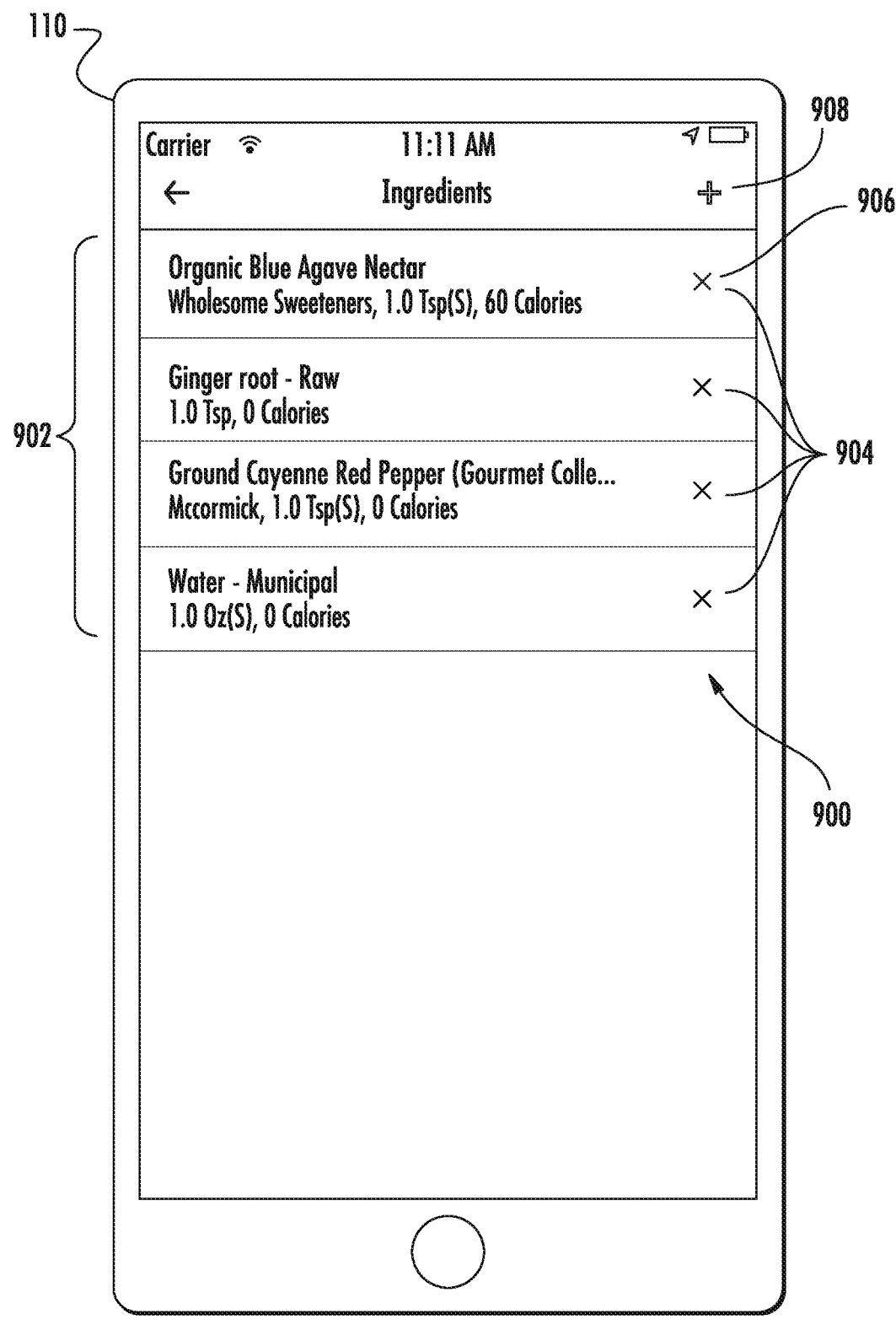
FIG. 9 shows an exemplary screen shot of a recipe view controller provided by the health tracking application and displayed on the personal electronics device of FIG. 2.

FIG. 9 shows an exemplary embodiment of a recipe ingredients view controller 900 for a food item. The recipe ingredients view controller 900 may be displayed when the user selects the more nutrition facts link 710 from the food summary view controller 700 (see FIG. 7) and the food item being viewed is a recipe instead of a food. In the recipe ingredients view controller 900, the user is presented with an ingredients list 902 comprising a number of ingredients 904 that are combined to make the recipe. Nutritional information for each ingredient 904 is provided below the ingredient. Additionally, the user may select the ingredient 904 in the ingredients list 902 to obtain additional nutritional information about the ingredient (similar to the nutritional information view controller 800 of FIG. 8). Furthermore, the user may choose to remove any ingredient in the list or add ingredients. In particular, if the user selects the "x" option 906 in the rightmost column of the ingredients list, the ingredient in that row will be removed from the recipe. Alternatively, if the user selects the "+" option 908 in the header, additional ingredients may be added to the recipe. In this manner, if the food item is a recipe for a "chicken sandwich", the user may easily add or remove ingredients from the chicken sandwich. For example, if the recipe includes "mustard" but not "mayonnaise", the user may remove the "mustard" ingredient and add "mayonnaise" to arrive at more complete nutritional data for the food item that he or she has consumed.

Method of Providing Nutritional Data for a User

Figure 10:
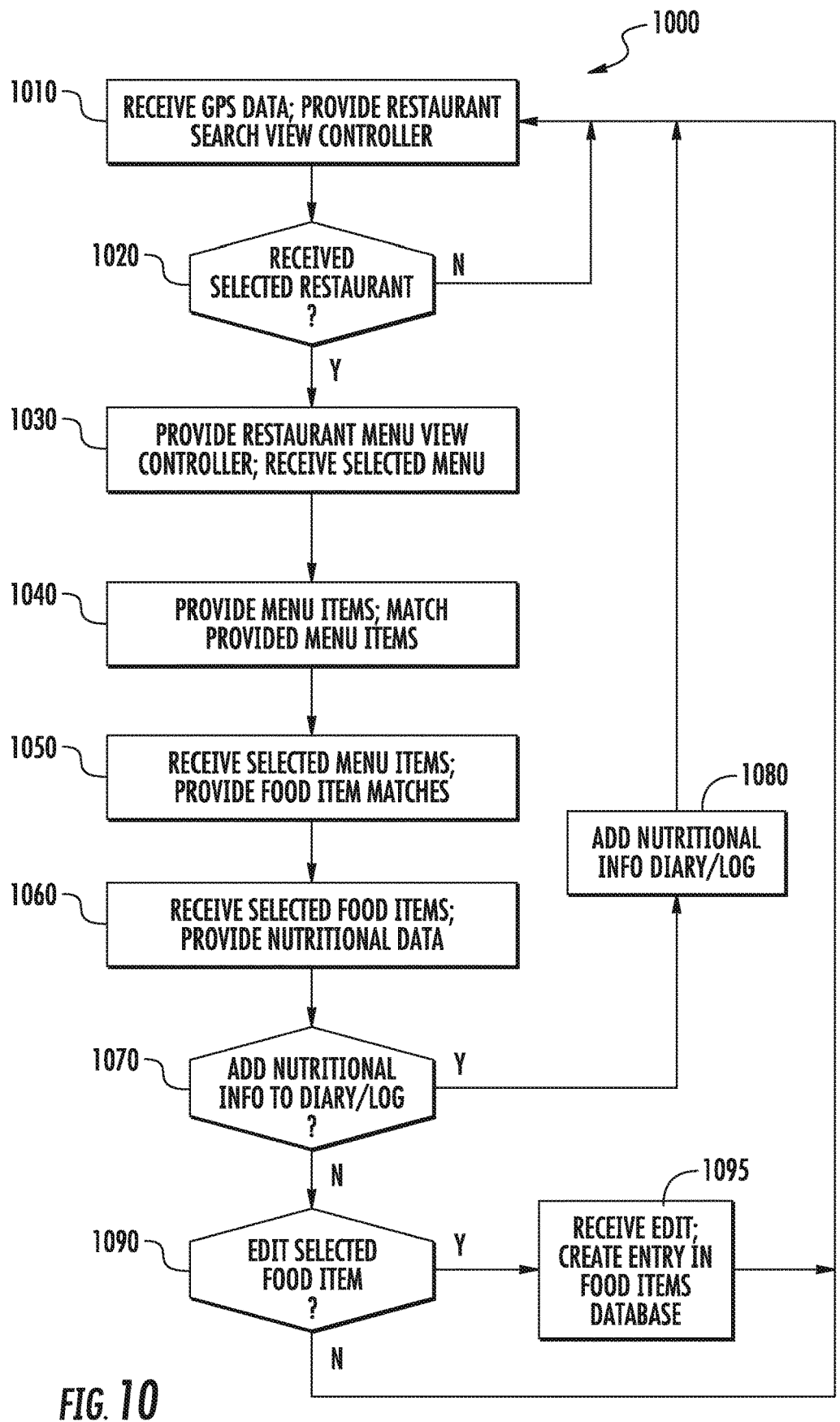
FIG. 10 shows a method of providing nutritional data for a user using the health tracking system of FIG. 1.

With reference now to FIG. 10, a method 1000 of providing nutritional data for a user using the health tracking application 248 is shown. The method begins with step 1010 wherein the health tracking application 248 receives GPS data from the personal electronic device 110 of the user. The health tracking application 248 then provides the restaurant search view controller to the user (e.g., the exemplary restaurant search view controller 400 of FIG. 4). The user then reviews the restaurants displayed on his or her personal electronic device 110 and selects one of the restaurants. As noted previously, the restaurants displayed are generally based on the location of the user but may also be based on a search term entered by the user (e.g., a genre of restaurant or a specific restaurant name). In at least one embodiment, the restaurant may deemed to be selected by virtue of the user's location within the premises of the restaurant or in proximity to the restaurant.

In step 1020 of FIG. 10, the health tracking application 248 determines whether a restaurant has been selected by the user. If no restaurant has been selected by the user, the health tracking application 248 continues processing at step 1010 and receives GPS data from the user. However, if a restaurant is selected by the user, the health tracking application 248 continues processing at step 1030.

At step 1030 of FIG. 10, the health tracking application 248 provides a restaurant menu view controller for the user (e.g., the exemplary restaurant menu view controller 500 of FIG. 5). The restaurant menu view controller allows the user to select a menu to view, wherein the viewed menu is associated with the restaurant. After the user selects one of the menus, the health tracking application 248 continues processing at step 1040.

At step 1040, the health tracking application 248 has received a selected menu from the user and a number of associated menu items from the selected menu are provided to the user such that the user may view the menu items on his or her personal electronics device 110. As the user reviews the menu items, the health tracking application 248 determines a number of matches for each menu item from the food items database 258. The matches are retained by the health tracking application 248, but are not displayed for the user until the user selects one of the menu items. In at least one alternative embodiment, the health tracking application 248 does not determine matches for the menu items until one of the menu items is selected by the user. After the user reviews the menu items on his or her personal electronic device 110, the user then selects one menu item that is closest to the menu item that he or she is interested in purchasing (or has already purchased).

At step 1050, the health tracking application 248 receives a selected menu item from the user and provides the determined matches for the selected menu item for the user to view on his or her personal electronic device 110 (e.g., exemplary matches for a selected menu item are shown in the match page 600 of FIG. 6). The user then selects one of these matches as the food item that best represents the food that he or she intends to consume. The health tracking application 248 continues processing at step 1060 and receives the selected match. The user is then presented with additional nutritional data about the selected match.

In step 1070, the user is given the option of adding the nutritional data for the selected match to his or her food diary/log for the day. Accordingly, if the user has consumed (or intends to consume) the selected match, and the nutritional data for the selected match appears to be appropriate for the food consumed, the user may simply make a selection to add this nutritional data to his or her food diary/log for the day (e.g., in the embodiment of FIG. 7, the user may select the "Add Item" option 712). If the user selects to add the nutritional data to the food diary/log, the health tracking application 248 continues processing at step 1080, and the nutritional information is added to the user's personal food diary/log. On the other hand, if the user does not wish to add the nutritional data for the selected food item to the user's personal food diary/log, the user may instead indicate that he or she wishes to edit the selected foot item at step 1090.

At step 1090 the health tracking app 248 determines whether the user wishes to edit the selected match (e.g., if the user has amended to serving size entry 705 or the number of servings entry 707 for the selected match and has selected the "add additional item" option 714). If the user has indicated that the user wishes to edit the selected match, the health tracking application 248 continues processing by moving to step 1095 and receiving the edit and creating a new entry in the food items database 258 for the edited food item. Any of various edits are possible. For example, in the embodiment of FIG. 7, a change to the serving size entry 705 or the number of servings entry 707 may result in the creation of a new food item. However, changes in any other nutritional data may also be entered as a new food item in the food items database 258. If the user does not indicate that he or she is interested in adding or editing the selected food item (i.e., in steps 1070 or 1090) after a given period of time, the user may be return to any previous view controller, or the health tracking app 248 may return the user to the restaurant search view controller, as noted in the exemplary embodiment of FIG. 10.

As an example of the above steps 1010-1095, consider the example of FIGS. 4-9 where the user is presented with a list of restaurants in the restaurant search view controller 400 of FIG. 4 and selects to view the menu of the nearby "Starbucks" restaurant. In FIG. 5, the user is presented with the Drinks menu from the "Starbucks" restaurant. The user then selects the "Cool Lime Starbucks Refreshers™ Beverage" menu item from the list of menu items 510 in FIG. 5. In association with selection of this menu item, the health tracking application 248 searches the food items database 258 and retrieves a list of possible food item matches. This list is presented on a match screen 600 of the restaurant menu view controller as shown in FIG. 6. The user then reviews these food item matches (shown in FIG. 6) to determine which of these matches most closely resembles what the user is interested in ordering (or has already ordered) from the restaurant. In this example, the user is interested in a 16 oz. Cool Lime Refreshers Beverage. The user is not interested in the 12 oz. ("Tall") option, the 24 oz. ("Venti") option, or the "Packet" option. Accordingly, the user selects the first match presented on the match screen of FIG. 6 (i.e., the 16 oz. "Cool Lime Refreshers Beverage"). The user is then presented with additional nutritional data in the restaurant food summary view controller 700 in the screen of FIG. 7. This screen provides the user with information about the selected match, including serving size, fat, carbohydrate, protein, calorie, or other information. If the user would like to post the selected food item to his or her Food Diary for the day, the user simply selects the "Add Item" option 712 to enter this food item into the Food Diary.

If the user wishes to amend the information for the selected food item and create a new item in the database, the user selects the "Add Additional Item" option 714, which allows the user to create a new food item in the MFP database based on the selected food item. Alternatively (or additionally), if any of the information about the food item is incorrect, the user may "Report the match as inaccurate" by selecting option 716. If the user wishes to view even more information about the food item before adding the food item to his or her food diary/log, the user selects the "More Nutrition Facts" link 710 and is presented with the restaurant food nutrition details view controller of FIG. 8. The restaurant food nutrition details view controller provides the user with additional data about the selected food item match. For example, as shown in FIG. 8, further information about fat, cholesterol, and other nutrition details about the exemplary 16 oz. "Cool Lime Starbucks Refreshers Beverage" may be obtained on this page. Further nutrition details about the food item may be presented to the user when the user scrolls down the page. Alternatively, if the matched food item is a "recipe" (instead of a "food"), the user may be presented with an additional selection that takes the user to a page similar to the restaurant recipe ingredients view controller 900 of FIG. 9.

As will be recognized by those of ordinary skill in the art, portions of the methods described herein may be implemented in suitable software code, such as the health tracking app 248, that may reside within ROM, RAM, a hard drive, other memory component, or a combination thereof. In some embodiments, computer instructions implementing an embodiment disclosed herein may be stored on a direct access storage device (DASD), magnetic device, disk device, optical storage device, or other appropriate computer-readable storage medium or storage device. A computer program product implementing an embodiment disclosed herein may therefore comprise one or more computer-readable storage media storing computer instructions translatable by processing circuitry/logic 232, a CPU, or other data processing device to perform an embodiment of a method disclosed herein.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer readable medium can be, by way of example, only but not by limitation, an electronic, magnetic, optical, electromagnetic, infrared, or semiconductor system, apparatus, system, device, or computer memory. The computer readable medium may include multiple computer readable media storing computer executable instructions, such as in a distributed system or instructions stored across an array.

The foregoing method may be accomplished with the assistance of a computer program, such as the health tracking app described above, stored in the memory and executed by the processor of the system server 230. The above described system and method solves a technological problem common in industry practice related to effective and efficient presentation of nutritional data to a user. Moreover, the above-described system and method improves the functioning of the computer/device by causing nutritional data to be easily presented to a user in a health tracking system, while also allowing the user to manipulate the nutritional data or otherwise make use of the nutritional data in the manner that he or she sees fit.

In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). Additionally, the phrases "in an embodiment," "in at least one embodiment," or "in embodiments," may each refer to one or more of the same or different embodiments. Furthermore, the terms "comprising," "including," "having," and the like, as used with respect to embodiments of the present disclosure, are synonymous.

The foregoing detailed description of one or more exemplary embodiments of the activity tracking device and associated display has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:
1. A method of providing nutritional data for a user, the method comprising:
receiving geo-location data for the user, the geo-location data sent from a personal electronic device associated with the user;
determining if the user is within a premises of a restaurant based on the geo-location data;
when the user is within the premises of the restaurant, receiving the restaurant as an automatically selected restaurant from a personal electronic device;
providing menu data for the user based on the selected restaurant;
receiving a selected menu item from the personal electronic device;
associating the selected menu item with a plurality of crowd-sourced food items in a database based at least in part on one or more of the plurality of crowd-sourced food items being previously selected in association with the selected menu item;
displaying the plurality of crowd-sourced food items for the user;
receiving a selected one of the plurality of crowd-sourced food items from the personal electronic device;
displaying nutritional data based on the selected one of the plurality of crowd-sourced food items;
receiving an edit from the user for the selected one of the plurality of crowd-sourced food items;

creating a new food item based on the received edit from the user for the selected one of the plurality of crowd-sourced food items; and prohibiting edits of the selected one of the plurality of crowd-sourced food items from the user when the user is not within the premises of the restaurant associated with the selected one of the plurality of crowd-sourced food items.

2. The method of claim 1 further comprising, before receiving the selected restaurant for the user, providing restaurant data for the user, the restaurant data based at least in part on the geo-location data.

3. The method claim 1 wherein the personal electronic device is a GPS enabled device.

4. The method of claim 1 wherein the plurality of crowd-sourced food items include food entries and recipe entries, wherein each of the recipe entries includes an editable list of ingredients, and each of the food entries does not include an editable list of ingredients.

5. The method of claim 1 wherein each of the plurality of crowd-sourced food items associated with the selected menu item is provided for display on the personal electronic device as a match, and wherein a predetermined number of matches are provided for each selected menu item.

6. A system for providing nutritional data to a user, the system comprising:

a personal electronic device configured to (i) receive geo-location signals and provide geo-location data for the user, (ii) display menu items, crowd-sourced food items, and nutritional data on a display device, and (iii) allow the user to select menu items and food items on the display device;

a database configured to store the food items and the nutritional data; and a data processing system configured to (i) receive geo-location data for the user from the personal electronic device, (ii) determine when the user is within a premises of a restaurant based on the geo-location data, (iii) when the user is within the premises of the restaurant, retrieve and display menu items associated with the restaurant to the user, (iv) receive menu items selected by the user, (v) associate the selected menu items with a plurality of food items in the database based at least in part on one or more of the plurality of food items being previously selected in association with the selected menu item, (vi) display the plurality of food items to the user on the display device, (vii) receive a selected food item from the user, the selected food item one of the plurality of food items displayed to the user, and (vii) display nutritional data to the user on the display device, the nutritional data associated with the selected food item; and (viii) prohibit edits to the selected food item when the user is not within the premises of the restaurant.

7. The system of claim 6 wherein the personal electronic device is a GPS enabled device.

8. The system of claim 6 wherein the data processing system is further configured to:

receive an edit from the user for the selected food item; and create a new food item in the database based on the received edit from the user.

9. The system of claim 8 wherein the plurality of food items include food entries and recipe entries, wherein each of the recipe entries includes an editable list of ingredients, and each of the food entries does not include an editable list of ingredients.

10. The system of claim 8 wherein the processor is further configured to:

prohibit edits when the user is not within the premises of the restaurant associated with the selected one of the plurality of food items.

11. The system of claim 6 wherein the data processing system is further configured to provide each of the plurality of food items as a match for the selected menu item, and provide a predetermined number of matches for each selected menu item.

12. A non-transient computer readable medium containing instructions for providing nutritional data by:

receiving geo-location data for the user, the geo-location data sent from a personal electronic device associated with the user;

determining if the user is within a premises of a restaurant based on the geo-location data;

when the user is within the premises of the restaurant, receiving the restaurant as a selected restaurant from a personal electronic device;

providing menu data for the user based on the selected restaurant;

receiving a selected menu item from the personal electronic device;

associating the selected menu item with a plurality of crowd-sourced food items in a database based at least in part the plurality of crowd-sourced food items being previously selected in association with the selected menu item;

providing the plurality of crowd-sourced food items for the user by displaying the plurality of crowd-sourced food items on a display for selection by the user;

receiving a selected one of the plurality of crowd-sourced food items from the personal electronic device;

providing nutritional data based on the selected one of the plurality of crowd-sourced food items; and prohibiting edits when the user is not within the premises of the restaurant associated with the selected one of the plurality of crowd-sourced food items.

13. The non-transient computer readable medium of claim 12 further containing instructions for providing nutritional data by:

providing restaurant data for the user, the restaurant data based at least in part on the geo-location data.

14. The non-transient computer readable medium of claim 12 wherein the personal electronic device is a GPS enabled device.

* * * * *